United States Patent
Kessels et al.

(10) Patent No.: US 9,895,474 B2
(45) Date of Patent: Feb. 20, 2018

(54) BREAST PUMP SYSTEM

(71) Applicant: KONINKLIJKE PHILIPS N.V., Eindhoven (NL)

(72) Inventors: Marijn Kessels, Eindhoven (NL); Wiecher Ferdinand Kamping, Rosmalen (NL); Arnold Aalders, Waalwijk (NL); Johannes Josephus Blaak, Sint Michielsgestel (NL); Cornelis Johannes Janson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 14/428,026

(22) PCT Filed: Sep. 12, 2013

(86) PCT No.: PCT/IB2013/058498
§ 371 (c)(1),
(2) Date: Mar. 13, 2015

(87) PCT Pub. No.: WO2014/045169
PCT Pub. Date: Mar. 27, 2014

(65) Prior Publication Data
US 2015/0250932 A1    Sep. 10, 2015

Related U.S. Application Data

(60) Provisional application No. 61/704,715, filed on Sep. 24, 2012.

(30) Foreign Application Priority Data

Sep. 24, 2012  (EP) .................................. 12185582

(51) Int. Cl.
*A61M 1/06* (2006.01)
*A61M 1/00* (2006.01)

(52) U.S. Cl.
CPC .......... *A61M 1/062* (2014.02); *A61M 1/0072* (2014.02); *A61M 1/06* (2013.01);
(Continued)

(58) Field of Classification Search
CPC ........ A61M 1/06; A61M 1/062; A61M 1/064; A61M 2210/1007; A61M 1/0031;
(Continued)

(56) References Cited

U.S. PATENT DOCUMENTS 5,007,899 A    4/1991  Larsson
5,902,267 A *  5/1999  Medo .................. A61M 1/0031
                                                              604/119
(Continued)

FOREIGN PATENT DOCUMENTS

DE    3508410 A1    9/1985
EP    0123269 A2   10/1984
(Continued)

*Primary Examiner* — Kevin C Sirmons
*Assistant Examiner* — Leah Swanson

(57) ABSTRACT

The present application relates to a breast pump system. The breast pump system comprises a vacuum path for creating a pressure reduction on a breast. A pump unit generates and releases a pressure reduction in the vacuum path, and comprises a vacuum pump (20). A leakage aperture (60) is configured to allow a controlled release of a pressure reduction in at least part of the vacuum path so that the pressure reduction in at least part of the vacuum path is released in the event that the pump unit fails to release the pressure reduction in the vacuum path. The vacuum pump (20) has a discharge port (22) for discharging air drawn from the vacuum path, and the leakage aperture (60) is disposed proximate to the discharge port (22) so that airflow dis-
(Continued)

charged from the discharge port (22) is directed over the leakage aperture (60).

13 Claims, 3 Drawing Sheets

(52) U.S. Cl.
CPC ............... *A61M 2205/3337* (2013.01); *A61M 2205/3344* (2013.01)

(58) Field of Classification Search
CPC .... A61M 1/066; A61M 1/068; A61M 1/0072; A61M 2205/3337; A61M 2205/3344
USPC ...................................................... 604/74, 75
See application file for complete search history.

(56) References Cited

U.S. PATENT DOCUMENTS

| | | | |
|---|---|---|---|
| 5,947,923 | A | 9/1999 | Uehara et al. |
| 6,290,671 | B1 | 9/2001 | Niederberger |
| 2004/0133151 | A1 | 7/2004 | Watanabe |
| 2008/0171970 | A1* | 7/2008 | Luzbetak ............ A61M 1/0049 604/74 |
| 2008/0177224 | A1* | 7/2008 | Kelly ................. A61M 1/0037 604/74 |
| 2012/0071820 | A1 | 3/2012 | Luzbetak |

FOREIGN PATENT DOCUMENTS

| | | | |
|---|---|---|---|
| EP | 0198469 | A2 | 10/1986 |
| EP | 2335750 | A1 | 6/2011 |

\* cited by examiner

BREAST PUMP SYSTEM

CROSS REFERENCE TO RELATED APPLICATIONS

This application is a national filing of PCT application Serial No. PCT/IB2013/058498, filed Sep. 12, 2013, published as WO 2014/045169 A1 on Mar. 27, 2014, which claims the benefit of U.S. provisional application Ser. No. 61/704,715 filed Sep. 24, 2012 and EP provisional application serial no. 12185582.9 filed Sep. 24, 2012, both of which are incorporated herein by reference.

FIELD OF THE INVENTION

The present invention relates to a breast pump system.

BACKGROUND OF THE INVENTION

A breast pump system is used for extracting milk from a breast of a user. A breast pump may be used if the baby or infant is not itself able to express milk from the breast, or if the mother is separated from the baby or infant, for example, if away from the baby at work. The use of a breast pump system to express milk may also be used to stimulate and increase milk production in women with a low milk supply.

Breast pump systems make use of a vacuum to induce milk expression from a nursing mother's breast. The pumping action of the device draws the milk from the nipple to a collection vessel, and the pressure and/or frequency may be adjustable to the preferences of the mother.

A breast pump system generally comprises a breast pump, acting as an expression unit, and an operating unit to operate the breast pump. The expression unit has a funnel in which a user's breast is receivable, and a receptacle in which the expressed milk is collected. The operating unit comprises a vacuum pump driven by a motor. The operating unit and the expression unit may be separated from each other and connected by a tube. Alternatively, the operating unit is mounted to the expression unit.

In use, the vacuum pump applies a vacuum to the breast received in the funnel. That is, when a user's breast is received in the funnel a sealed air system is created between the user's breast and the vacuum pump so that the vacuum pump is able to generate a vacuum which acts on the user's breast. In one arrangement, the vacuum in the funnel is created indirectly. The reduction in pressure generated by the vacuum pump acts on a membrane received in a chamber in the expression unit which deforms to cause a reduction in pressure in the funnel. Therefore, a vacuum is applied to the breast which induces milk to be expressed.

It is known to provide a breast pump system in which a cyclical pressure differential is applied to the breast. In such an arrangement, a pressure release valve is disposed in the operating unit. After a desired reduction in pressure has been established, the valve is opened to allow the vacuum acting on the membrane to be released. As the pressure from the vacuum is released, the membrane deforms back into its original position and the vacuum acting on the user's breast is reduced. By cyclically opening and closing the valve a cyclic pressure profile in order to express milk from the breast is achieved.

However, one problem with the above arrangement is that if the valve fails to open then the vacuum acting on the user's breast is maintained which may cause discomfort or injury to a user and/or may prevent the user from removing their breast from the vacuum pump.

SUMMARY OF THE INVENTION

It is an object of the invention to provide a breast pump system which substantially alleviates or overcomes the problems mentioned above.

According to the present invention, there is provided a breast pump system comprising a vacuum path for creating a pressure reduction on a breast, a pump unit configured to generate and release a pressure reduction in the vacuum path, comprising a vacuum pump configured to generate a pressure reduction in the vacuum path, and a leakage aperture configured to allow a controlled release of a pressure reduction in at least part of the vacuum path so that the pressure reduction in at least part of the vacuum path is released in the event that the pump unit fails to release the pressure reduction in the vacuum path, wherein the vacuum pump has a discharge port for discharging air drawn from the vacuum path, the leakage aperture being disposed proximate to the discharge port so that airflow discharged from the discharge port is directed over the leakage aperture.

This means that a vacuum is not maintained in the vacuum path in the event that the pressure release valve fails. For example, should the release valve fail to open when a vacuum in the vacuum path is acting on a user's breast, then the leakage aperture acts as a fail safe to ensure that the vacuum acting at the breast is released in a controlled manner. Therefore, this vacuum release prevents a user from concern, and/or prevents pain or damage to a user if the user attempts to pull the breast pump away from the breast with a high force.

It is noted that EP 0 198 469 A2 discloses a breast pump which has a vent opening defined in a vent neck. The vent neck is directed rearwardly with respect to a mouth portion of a flange for receiving a breast, and is located approximately perpendicular to a hose connector receiver at a neck portion. The specific arrangement of the vent opening allows a user of the breast pump to easily cover the opening with a thumb. When the user removes her thumb from the vent opening, air is allowed to enter through a vent bore and vacuum bore, allowing air pressure within a collection container, the neck portion and a throat portion of the flange to increase to equal the pressure surrounding the exterior of the flange, thereby permitting the flange and the breast to relax.

An advantage of the arrangement according to the present invention in which the leakage aperture is disposed proximate to the discharge port of the vacuum pump is that the air flow directed over the leakage aperture acts to keep the leakage aperture free from any detritus that may restrict the flow of air therethrough.

As mentioned, the pump unit may further comprise a pressure release valve operable to release a pressure reduction in the vacuum path.

At least part of the vacuum path may be formed by a tube and the leakage aperture may be formed in the tube.

An advantage of this arrangement is that the leakage aperture may be easily formed. The leakage aperture may be formed without any additional components. Furthermore, an optimal position of locating the leakage aperture may be determined.

The leakage aperture may be formed by a bore extending through a sidewall of the tube. Therefore, a simple manufacturing method for forming the hole is achievable.

The breast pump system may further comprise a connector to which the tube is attachable. The leakage aperture may be formed in the connector. This means that the leakage aperture is formed in a rigid component and so deformation is restricted. Therefore, the size of the aperture may be accurately determined and so the speed of release of the pressure reduction can be accurately determined.

The leakage aperture may be a channel formed in the connector. The tube, or a hose attachable to the connector to form part of the vacuum path, may be configured to partially overlap the channel when attached to the connector so that the channel communicates between the vacuum path and atmosphere. This means that the leakage aperture is easy to implement.

The leakage aperture may be formed in the pressure release valve.

The leakage aperture may be formed in the vacuum pump.

A filter material may extend across the leakage aperture. Therefore, potential blockages of the leakage aperture are reduced.

The leakage aperture may be formed by an insert with a bore extending between the vacuum path and atmosphere. This means that the size of the leakage aperture may be determined and manufactured to tight tolerances.

The insert may be disposed in the tube. Therefore, the insert resists restriction of the leakage aperture if the tube deforms.

The breast pump system may further comprise a chamber forming part of the vacuum path and a membrane disposable in the chamber to separate the vacuum path into a first section and a second section, wherein the membrane may be deformable in response to a reduction of pressure in the first section to generate a reduction of pressure in the second section. Therefore, an indirect pressure reduction is able to be formed at a user's breast. That is, milk expressed from a user's breast is prevented from flowing in the first section of the vacuum path.

The leakage aperture may be configured to allow a controlled release of a pressure reduction generated in the first section of the vacuum path. This means that the leakage aperture does not come into contact with milk. Therefore, the first section does not have to be cleaned/washed. A small droplet of water or milk in the leakage aperture which could block the aperture would not be visible in the aperture. The positioning of the leakage aperture in the first section means that the membrane is able to return to its neutral condition in the event the pressure release valve fails. This may prevent damage to the membrane in the event that the vacuum pump starts to operate again.

The second section of the vacuum path may be formed between the membrane and a funnel for receiving a user's breast.

The breast pump system may further comprise an operating unit and an expression unit, wherein the leakage aperture is disposed in the operating unit.

The operating unit may comprise a housing, and the leakage aperture may be disposed in the housing. Therefore, a user and/or detritus are restricted from being able to block the leakage aperture.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
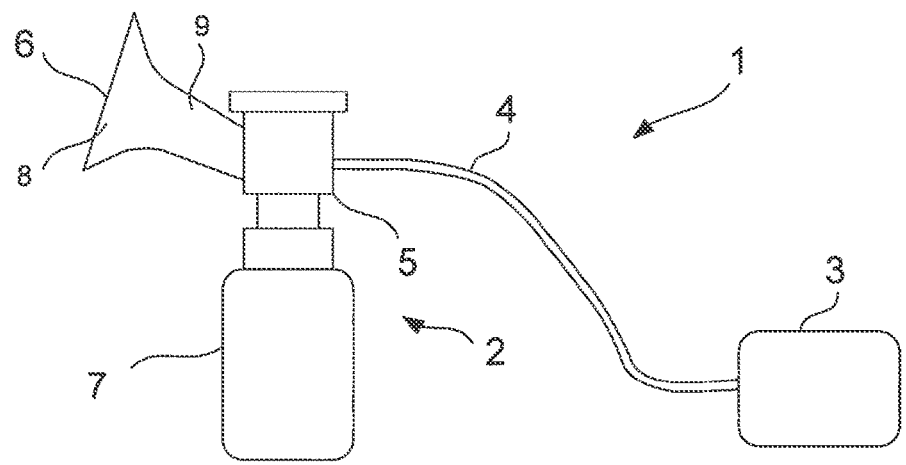
FIG. 1 is a diagrammatic side view of a breast pump system.

A breast pump system is shown in FIG. 1. The breast pump system 1 comprises a breast pump 2, also known as an expression unit, and an operating unit 3.

The breast pump 2 and the operating unit 3 are connected by a hose 4. The hose 4 provides a fluid communication between the breast pump 2 and the operating unit 3. The hose 4 may also be used to provide an electrical connection between the breast pump 2 and the operating unit 3. For example, the hose 4 may supply an operating signal or electrical power between the breast pump and the operating unit. In an alternative embodiment, the operating unit 3 is directly mounted and connected to the main body 5.

The breast pump 2 has a main body 5, a funnel 6 and a collection vessel 7. The collection vessel 7, or receptacle, collects milk expressed from a user's breast and may take the form of a feeding bottle or bag. The collection vessel 7 is attached to the main body 5 by a screw fitting, although it will be understood that alternative releasable attachment means may be used, such as clips (not shown).

The breast-receiving funnel 6 extends from the main body 5. The funnel 6 is configured to receive the breast of a user. The funnel 6 has a mouth 8 and a throat 9. The mouth 8 is open at an outer end of the funnel 6 to receive a user's breast, and the funnel 6 converges from the outer end towards the throat 9 to form a hollow recess in which a breast is received.

The main body 5 fluidly connects the funnel 6 to the collection vessel 7. A fluid passageway 10 (refer to FIG. 2) is formed through the main body 5 from the breast receiving space of the funnel 6 to the collection vessel 7. The main body 5 is formed from an outer shell. The main body 5 is integrally formed with the funnel 6, however it will be understood that the funnel 6 may be detachable. In the present arrangement, the main body 5 is formed from polypropylene, although it will be understood that alternative suitable materials may be used.

Figure 2:
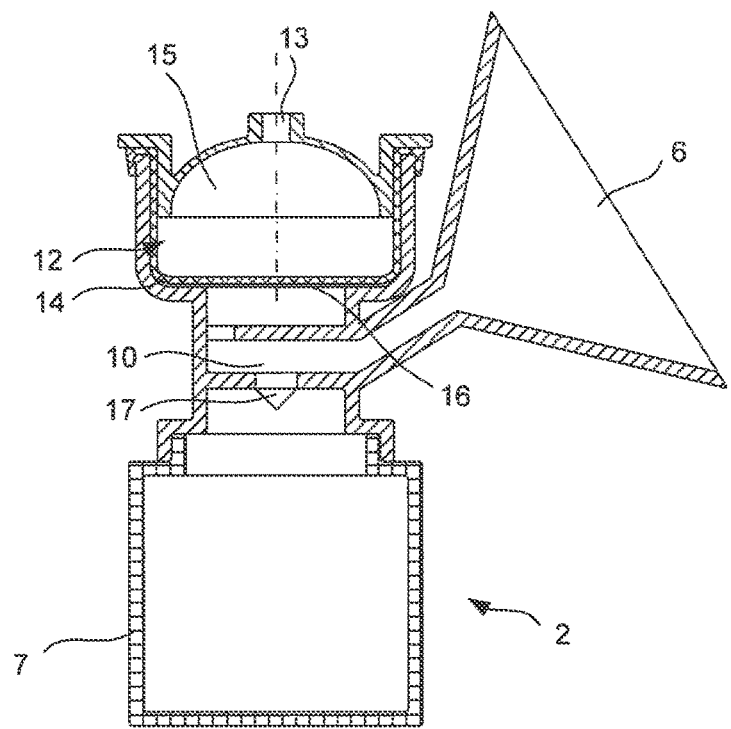
FIG. 2 is a diagrammatic cross-sectional side view of a breast pump of a breast pump system as shown in FIG. 1.

Referring now to FIG. 2, a chamber 12 is formed in the main body 5. The chamber forms part of a vacuum path. The chamber 12 is in fluid communication with the fluid passageway 10 between the funnel 6 and the collection vessel 7. The chamber 12 has a vacuum port 13. The vacuum port 13 provides a port to communicate with the operating unit 3. The hose 4 is mountable to the vacuum port 13 to fluidly connect the chamber 12 with the operating unit 3.

A membrane 14 is received in the chamber 12. The membrane 14, also known as a diaphragm, is flexible. An outer rim of the membrane 14 is mounted to the chamber 12. The membrane 14 separates the chamber 12 into a first space 15 and a second space 16. The first space 15 communicates with the vacuum port 13. The first space 15 forms part of a first section of the vacuum path. The second space 16 communicates with the fluid passageway 10 between the breast receiving space of the funnel 6 and the collection vessel 7. The second space 16 forms part of a first section of the vacuum path. A one-way valve 17 is disposed in the fluid passageway 10. The one-way valve prevents a pressure reduction being formed in the collection vessel 7. The membrane 14 is formed from silicone. However, it will be understood that the membrane 14 may be formed from another suitable material.

The flexible membrane 14 has a predefined shape. In the present arrangement, the membrane 14 has a substantially cup-shaped arrangement in a neutral condition. That is, when the membrane 14 is received in the chamber 12, but has not been deformed. However, it will be understood that the membrane 14 may have an alternative shape.

The operating unit 3 comprises a controller (not shown), a power source (not shown), a motor (not shown) and a pump unit. The pump unit is configured to generate and release a pressure reduction in the vacuum path. The controller controls operation of components of the operating unit 3. The means for generating the pressure reduction and the means for releasing the pressure reduction are separate components. However it will be understood that the means for generating the pressure reduction and the means for releasing the pressure reduction may be integrally formed. In particular, in the present embodiment the pump unit comprises a vacuum pump 20 and a pressure release valve 30. The vacuum pump 20 acts as a pressure reduction means. The pressure release valve 30 acts as a means for releasing an increase or reduction in pressure.

The vacuum pump 20 is configured to generate a pressure reduction in a vacuum path to operate the breast pump 2. That is, the vacuum pump produces a vacuum. The vacuum pump 20 has an intake port 21 and a discharge port 22. The vacuum pump 20 draws air in through the intake port 21 and discharges air from the discharge port 22. The intake port 21 is a tubular part extending from the vacuum pump body.

The release valve 30 is configured to cyclically open to release a vacuum generated by the vacuum pump. By cyclically opening and closing the valve a cyclic pressure profile is achieved. The pressure release valve 30 opens to atmosphere. The pressure release valve 30 may be a solenoid valve. Operation of the pressure release valve 30 is controlled by the controller. The pressure release valve 30 has an inlet port 31. The inlet port 31 is a tubular part extending from the valve body. The inlet port 31 has a shoulder 32 on its outer surface (refer to FIG. 7).

Figure 3:
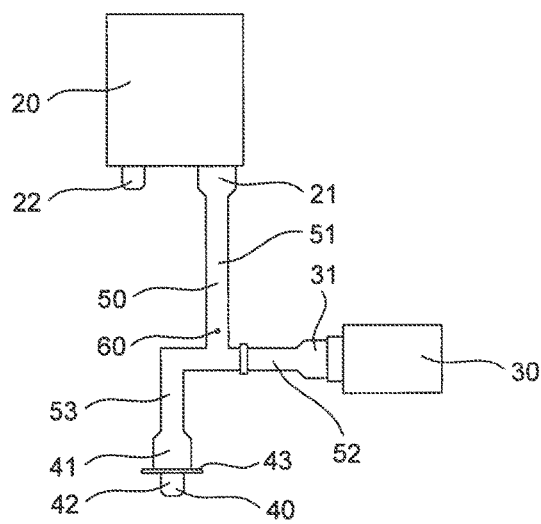
FIG. 3 is a diagrammatic view of a vacuum pump, a pressure release valve and a tube communicating between the vacuum pump and release valve forming part of the breast pump system shown in FIG. 1.
Figure 6:
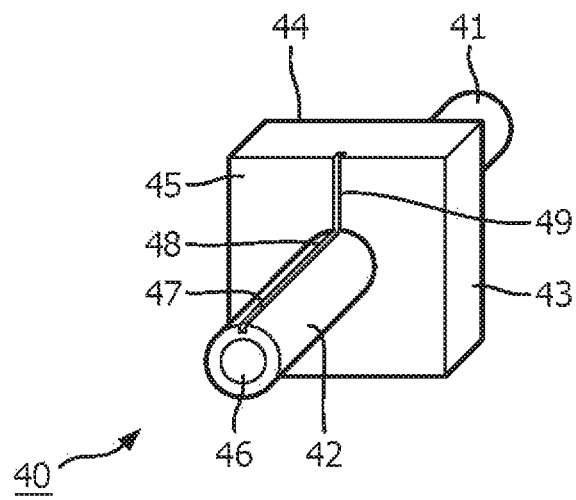
FIG. 6 is a diagrammatic perspective view of a connector of the breast pump system shown in FIG. 2.

A connector 40 is mounted to the housing of the operating unit 3 (refer to FIGS. 3 and 6). The connector 40 has an internal port 41 and an external port 42. The connector 40 is mounted to the housing of the operating unit 3 and extends therethrough. The internal port 41 protrudes in the housing and the external port 42 protrudes from the housing. The connector 40 also has a collar 43. The collar 43 is disposed between the internal port 41 and the external port 42. The internal port 41 protrudes from a first face 44 of the collar 43 and the external port 42 protrudes from a second face 45 of the collar 43. A bore 46 extends through the connector 40, between ends of the internal and external ports 42, 43. Therefore, a passage is formed through the connector 40. The connector 40 acts as an attachment point for one end of the hose 4. That is, the connector 40 acts to connect the hose 4 to the operating unit 3. The connector 40 is formed from a thermoplastic, such as Acrylonitrile butadiene styrene (ABS). However, it will be understood that the connector 40 may be formed from another suitable material.

A tube 50, acting as an air passage, fluidly communicates between the vacuum pump 20, the pressure release valve 30 and the connector 40. The tube 50 is formed from a resilient material, such a deformable rubber material. However, it will be understood that the tube 50 may be formed from another suitable material.

Figure 4:
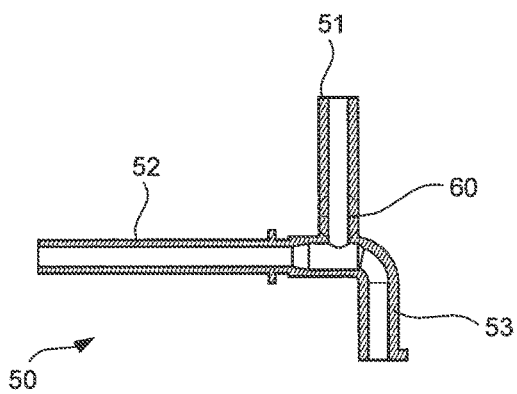
FIG. 4 is a diagrammatic cross-sectional view of the tube shown in FIG. 3.
Figure 5:
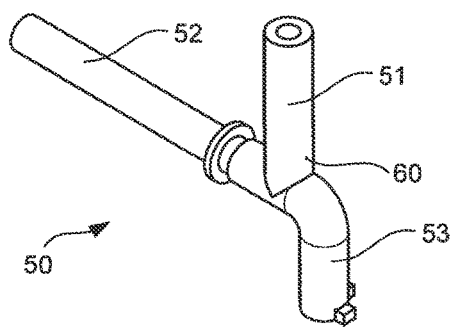
FIG. 5 is a diagrammatic perspective view of the tube shown in FIG. 3.

The tube 50 has a first arm 51, a second arm 52 and a third arm 53. Each of the arms defined a passageway. The arms 51, 52, 53 of the tube 50 are in fluid communication with each other. As shown in FIGS. 3 to 5, the first arm 51 forms a junction with the second arm 52 at one end of the second arm 52, and the third arm 53 forms a junction with the second arm 52 proximate to that end. However, it will be understood that alternative arrangements of the tube 50 are envisaged. The arms 51, 52, 53 are integrally formed.

Each of the arms is open at one end. When the operating unit 3 of the breast pump system 1 is assembled, the tube 50 is attached to each of the vacuum pump 20, the pressure release valve 30 and the connector 40. That is, the tube 50 fluidly communicates with each of the vacuum pump 20, the pressure release valve 30 and the connector 40.

An open end of the first arm 51 is attached to the intake port 21 of the vacuum pump 20. The tube 50 is formed from a resilient material. The inner diameter of the end of the tube 50 is slightly smaller than the outer diameter of the intake port 21 of the vacuum pump 20. Therefore, the end of the tube 50 is able to expand to fit over the intake port 21 of the vacuum pump 20 to form a push fit therewith. This means that the end of the tube 50 is mounted to the vacuum pump 20. The tube 50 is then in fluid communication with the vacuum pump 20.

An open end of the second arm 52 is attached to the inlet port 31 of the pressure release valve 30. The tube 50 is formed from a resilient material. The inner diameter of the end of the tube 50 is slightly smaller than the outer diameter of the inlet port 31 of the pressure release valve 30. Therefore, the end of the tube 50 is able to expand to fit over the inlet port 31 of the pressure release valve 30 to form a push fit therewith. This means that the end of the tube 50 is mounted to the pressure release valve 30. The tube 50 is then in fluid communication with the pressure release valve 30.

An open end of the third arm 53 is attached to the internal port 41 of the connector 40. The tube 50 is formed from a resilient material. The inner diameter of the end of the tube 50 is slightly smaller than the outer diameter of the internal port 41 of the connector 40. Therefore, the end of the tube 50 is able to expand to fit over the internal port 41 of the connector 40 to form a push fit therewith. This means that the end of the tube 50 is mounted to the connector 40. The tube 50 is then in fluid communication with the connector 40.

The vacuum pump 20, the pressure release valve 30, the connector 40 and the tube 50 are received in the housing of the operating unit 3 of the breast pump system 1. The connector 40 is mounted to the housing of the operating unit 3, with the internal port 41 (to which the tube 50 is attached) received in the housing and the external port 42 protruding from the housing. The housing acts to protect the components received therein. The discharge port 22 of the vacuum pump 20 discharges to atmosphere in the housing.

When the breast pump system 1 is assembled, the hose 4 extends between the operating unit 3 and the breast pump 2. That is, the operating unit 3 and breast pump 2 are in fluid communication with each other through the hose 4. The hose 4, acting as an external tube, is attached to the connector 40.

In the present embodiment, the hose 4 is formed from a resilient material. The inner diameter of the hose 4 is slightly smaller than the outer diameter of the external port 42 of the connector 40. Therefore, the end of the hose is able to expand to fit over the external port 42 of the connector 40 to form a push fit therewith. This means that the end of the hose 4 is mounted to the connector 40. The hose 4 is then in fluid communication with the connector 40. This means that the hose 4 is in fluid communication with the vacuum pump 20 and the pressure release valve 30.

Similarly, the inner diameter of the hose 4 is slightly smaller than the outer diameter of the vacuum port 13 of the breast pump 2. Therefore, the other end of the hose 4 is able to expand to fit over the vacuum port 13 of the breast pump 2 to form a push fit therewith. This means that the end of the hose 4 is mounted to the breast pump 2. The hose 4 is then in fluid communication with the chamber 12. Therefore, the chamber 12 is in fluid communication with the vacuum pump 20 and the pressure release valve 30.

In the present embodiment, the connector 40 fluidly communicates the hose 4 extending from the operating unit 3 and the tube 50 in the operating unit 3. However, it will be understood that in an alternative arrangement the connector 40 may be omitted and the tube 50 may connect directly to the vacuum port 13. In such an embodiment, the tube may extend through the housing.

Although in the present embodiment separate breast pump and operating units are provided, in other embodiments the breast pump system components such as the collection vessel, funnel, vacuum pump, electric motor, power supply, pressure release valve and tube may be housed in a single body. For example, components of the operating unit may be integrated into the main body of the breast pump, removing the need for a separate operating unit.

In the present arrangement, the tube 50 defines at least part of a vacuum path. That is, when the tube 50 is attached to the vacuum pump 20, the vacuum pump 20 acts to generate a pressure reduction in the passage or passages in the tube 50 by drawing air from the tube 50. The intake port 21 of the vacuum pump also forms part of the vacuum path. However, it will be understood that the intake port 21 may be omitted, for example if the tube is attached to the vacuum pump 20 by other means, or the tube 50 is integrally formed with the vacuum pump 20.

Similarly, the pressure release valve 30 also forms part of the vacuum path. In the present arrangement, the inlet valve 31 of the pressure release valve 30 forms part of the vacuum path, although the intake port 21 may be omitted, for example if the tube is attached to the vacuum pump 20 by other means. The connector 40 also forms part of the vacuum path, although the connector 40 may be omitted.

When the breast pump system 1 is assembled, such that the operating unit 3 is in fluid communication with the breast pump 2, the hose 4, chamber 12, fluid passageway 10 and funnel 6 form part of the vacuum path. That is, the hose 4, chamber 12, fluid passageway 10 and funnel 6 are in fluid communication with the vacuum pump 20 so that the vacuum pump 20 acts to generate a pressure reduction in each of the hose 4, chamber 12, fluid passageway 10 and funnel 6.

In the present embodiment, it will be understood that the fluid passageway 10 and funnel 6 are in indirect fluid communication with the vacuum pump 20 and pressure release valve 30. That is, the membrane extends across the chamber, and so separates the vacuum path into the first section and the second section. The first section is defined between the vacuum pump 20, pressure release valve 30 and membrane 14. The second section is defined between the membrane 14 and the funnel 6. When the membrane 14 deforms in response to a pressure reduction being formed in the first section, a corresponding pressure reduction may be generated in the second section.

It will be understood that in an alternative arrangement, the fluid passageway 10 and funnel 6 may be in direct fluid communication with the vacuum pump 20 and pressure release valve 30. That is, the membrane is omitted.

A leakage aperture 60 is formed to allow a controlled release of a pressure reduction in the vacuum path. Therefore, the pressure reduction in the vacuum path is released in the event of failure of the pressure release valve 30. The leakage aperture is in constantly in an open condition. That is, the leakage aperture is configured to allow a continuous flow of air into the vacuum passage.

The leakage aperture 60 is formed in the tube 50. The leakage aperture 60 is a hole formed through the tube 50. The leakage aperture 60 extends between the inner and outer surfaces of the tube 50. In the present embodiment, the leakage aperture 60 is in the first arm 51 of the tube 50. However, it will be understood that the leakage aperture 60 may be disposed in an alternative position on the tube 50.

The leakage aperture 60 is formed by use of laser cutting. However, it will be understood that alternative forming means may be used. It will be understood that the flow rate is dependent on the dimensions of the leakage aperture 60. It will be understood that the leakage aperture forms part of a safety system. The leakage aperture 60 is configured so that it cannot be closed, or adjusted. Therefore, it is not possible to adjust the system to prevent the aperture acting to release a reduction in pressure or negate the action of the vacuum pump.

In use, a user's breast is received in the funnel 6 and forms a fluid seal between the funnel 6 and the breast. The user's nipple is received in the funnel 6. When the breast pump is operated, the controller (not shown) operates the motor (not shown) to operate the vacuum pump 20 and pressure release valve 30.

The vacuum pump acts to generate a pressure reduction in the vacuum path. That is, the vacuum pump 20 acts to generate a pressure reduction in the first section of the vacuum path by drawing air from the tube 50 in through the intake port 21 and discharging it to atmosphere through the discharge port 22. When a vacuum condition is produced in the first section of the vacuum path, the membrane 14 is induced to deform in the chamber 12.

The distension of the membrane 14 causes a pressure reduction in the second section of the vacuum path. As a breast is received in the mouth 8 of the funnel 6, and forms a fluid seal therewith, a pressure reduction is caused in the second section of the vacuum path a vacuum acts on the user's breast to induce the expression of milk from a user's nipple which is received in the funnel 6.

Although the leakage aperture 60 in the tube 50 and communicating between the vacuum path and atmosphere is open, the area of the leakage aperture is small enough that the leakage aperture does not have a substantive effect on the reduction of pressure in the vacuum path during operation of the breast pump. That is, the rate of air flow through the aperture is restricted so that the desired operating pressure reduction at the user's breast to induce milk expression is obtained.

During normal operation, the controller operates the pressure release valve to release the reduction in pressure in the first section of the vacuum path when a predetermined pressure reduction is achieved. When the vacuum is released in the first section of the vacuum path, the membrane 14 is urged to return to its neutral condition. This causes the vacuum in the second section of the vacuum path, and therefore at the user's breast, to be released. The controller then closes the pressure release valve and a reduction in pressure is again generated in the vacuum path.

The vacuum is applied to the breast at intervals. That is, the reduction in pressure is generated on a cyclic basis. After a vacuum has been established, the pressure release valve is temporarily opened to increase the pressure in the vacuum path. Thus, the breast pump uses a cyclic pressure profile in order to express milk from the breast.

In normal operation the vacuum should be released after each pumping cycle, by opening the release valve. The pressure release valve may be a mechanical or an electro-mechanical valve, for example a solenoid valve. However, if for any other reason the vacuum has not been released, or is only partially released, for instance because the release valve has failed to open or an inlet to the valve has become blocked, a pressure reduction is maintained in the vacuum path.

Specifically, if the vacuum is not released when the vacuum pump is stopped, a reduction in pressure continues to act on the user's breast received in the funnel. Therefore, the user is not able to easily remove their breast from the vacuum pump. However, the leakage aperture 60 provides a path for air to flow into the vacuum path to release the pressure reduction. That is, the leakage aperture 60 provides a means to release a vacuum acting on a user's breast in the event of failure of the pressure release valve 30. It will be understood that the aperture is in a constantly open condition. That is the leakage aperture 60 cannot be closed. Therefore, the aperture allows a small flow of air therethrough into the vacuum pathway at all times. The leakage aperture is sufficiently small that it does not hinder the pump unit from obtaining the required pressure reduction in the vacuum pathway when the vacuum pump is operated, but does provide a means of releasing the reduction of pressure in the event that the pump unit fails. The leakage aperture 60 is configured to provide a release in the vacuum within a maximum time of 15 seconds.

Therefore, discomfort or injury to the user due to a vacuum being maintained at the user's breast is prevented. Furthermore, the user will not be concerned due to being unable to remove their breast from the breast pump.

The leakage aperture is unrestricted. That is, is not restricted to prevent the flow of air therethrough from atmosphere into the vacuum path at any stage, although the flow rate of air through the leakage aperture is restricted so that it does not affect normal operation of the breast pump. Therefore, it is not possible for the leakage aperture to be blocked, and so the vacuum is not prevented from being released in the event of failure of the vacuum pump.

In the present arrangement, in which the funnel is in indirect fluid communication with the vacuum pump, the leakage aperture 60 is formed to allow air flow into the first section of the vacuum path. Therefore, the leakage aperture 60 allows a release of the pressure reduction in the first section, therefore enabling the membrane to return to its neutral position. When the membrane returns to its neutral position, it will be understood that the pressure reduction in the second section is released, so that a user is able to remove their breast from the funnel. An advantage of this arrangement is that it allows the membrane to return to its neutral condition in the event of the vacuum release valve failing. However, it will be understood that in an alternative arrangement the leakage aperture 60 is formed to allow air flow into the second section of the vacuum path. However, in such an arrangement the aperture is configured so that it cannot be closed, or adjusted. Therefore, it is not possible to adjust the system to prevent the aperture from acting as part of a safety system.

The arrangement of the leakage aperture means that the leakage aperture is easily formed during manufacture. The arrangement of the leakage aperture also ensures that no additional components are required.

The leakage aperture is configured to continuously allow the flow of air therethrough into the vacuum path. Therefore, it is not necessary for a user to do anything in order for the vacuum to be released so that the user is able to remove their breast from the funnel.

According to the present invention, the leakage aperture 60 is disposed so that airflow discharged from the discharge port 22 is directed over the leakage aperture 60. That is, the discharge port 22 and the leakage aperture 60 are configured to be arranged in proximity to each other so that an airflow is generated over the exposed part of the leakage aperture 60. The air flow directed over the leakage aperture acts to keep the leakage aperture free from any detritus that may restrict the flow of air therethrough. The leakage aperture 60 may also, or in addition, have a filter disposed over it to prevent blockage of the airway.

Another embodiment of the breast pump system will now be described with reference to FIG. 6. The features of this aspect of the breast pump system can be implemented in any of the breast pump systems described above with reference to FIGS. 1 to 3, or in any conventional breast pump system not including the features of the above-described systems. The general arrangement is described above and so a detailed description will be omitted herein.

In FIG. 6 the connector 40 of the present embodiment is illustrated. In the present embodiment, the hole in the tube, acting as the leakage aperture, is omitted. However, the leakage aperture is formed in the connector 40. The connector 40 has a channel 47 acting as the leakage aperture. The channel 47 is formed in the external port 42 of the connector 40. The channel 47 also extends in the second face 45 of the collar 43. The channel 47 extends to the free end of the external port 42. In this embodiment, the channel 47 is an elongate recess formed in the surface of the connector 40. A first portion 48 of the channel 47 extends from the free end of the external port 42 to the collar 43, and a second portion 49 of the channel 47 extends from the first portion 48 to an edge of the collar 43.

When the hose 4 is attached to the connector 40, the end of the hose 4 overlaps the first portion 48 of the channel 47. The first portion 48 of the channel is open at the free end of the external port 42 to the vacuum path defined in part by the hose 4 when the hose is attached to the connector 40. The channel 47 is open to the atmosphere due to the second portion 49 of the channel 47. The second portion of the channel formed in the collar 43 prevents the channel from being blocked by the hose 4. Therefore, air is able to pass from the second portion 49 of the channel 47, along the first portion 48 and into the vacuum path defined in part by the hose 4. This means that the reduced pressure in the vacuum path is able to be released.

Although in the above embodiment the channel 47 acting as the leakage aperture is formed in the external port 42 of the connector 40, such that the hose 4 partially overlaps the channel 47, it will be understood that in an alternative arrangement the channel acting as the leakage aperture is formed in the internal port 41 of the connector 40. In such an arrangement, the first portion of the channel is formed in the outer surface of the internal port 41 and the second portion of the channel is formed in the first face 44 of the collar 43. Therefore, when the tube 50 is attached to the connector 40, the free end of the third arm 53 of the tube 50 overlaps the first portion of the channel. Therefore, air is able to pass along the portion of the channel in the internal port 41 and into the vacuum path defined in part by the tube 50. This means that the reduced pressure in the vacuum path is able to be released. An advantage of this arrangement is that the exposed section of the leakage aperture is disposed in the housing of the operating unit and so it is not possible for a user to accidentally block the aperture.

Although in the above described embodiment the leakage aperture is formed in the connector by the channel, it will be understood that alternative arrangements are possible. For example, the leakage aperture may be formed by a hole formed through the connector. Such a hole may be formed through the internal or external ports 41, 42, or through the collar 43 to communicate with the passage 46 formed through the connector. Therefore, the vacuum path defined in part by the connector is able to communicate with atmosphere. In an arrangement in which the hole is formed through the internal or external ports 41, 42, a shoulder may be positioned to prevent the tube 50 or hose 4 respectively blocking the leakage aperture.

Another embodiment of the breast pump system will now be described with reference to FIG. 7. The features of this aspect of the breast pump system can be implemented in any of the breast pump systems described above with reference to FIGS. 1 to 3, or in any conventional breast pump system not including the features of the above-described systems. The general arrangement is described above and so a detailed description will be omitted herein.

Figure 7:
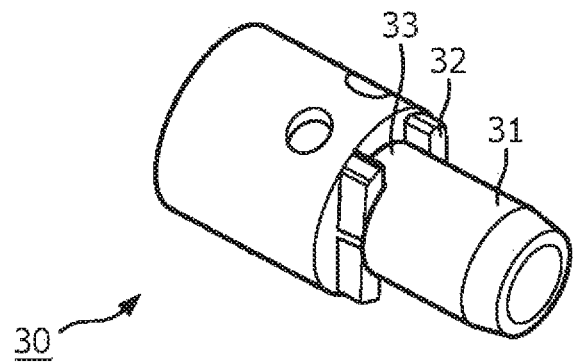
FIG. 7 is a partial view of a release valve shown in FIG. 3.

In FIG. 7 the inlet port 31 of the pressure release valve 30 is illustrated. In the present embodiment, the hole in the tube, acting as the leakage aperture, is omitted. However, a hole, acting as a leakage aperture 33, is formed through the inlet port 31 of the pressure release valve 30. Therefore, the vacuum path defined in part by the inlet port 31 of the pressure release valve 30 is able to communicate with atmosphere. A shoulder 32 is formed on the inlet port 31. The shoulder 32 upstands from inlet port 31. The exposed part of the leakage aperture 33 is positioned in a recess defined by the shoulder 32. Alternatively, the exposed part of the leakage aperture 33 is positioned on the shoulder 32. Therefore, the leakage aperture 33 is positioned to prevent the tube 50 blocking the leakage aperture 33. That is, when the tube 50 is attached to the inlet port 31, the shoulder 32 prevents the end of the tube 50 from overlapping the leakage aperture 33 and so preventing the flow of air therethrough.

Although in the present embodiment the leakage aperture is formed by a hole formed through the inlet port 31, it will be understood that a leakage aperture may be formed in the pressure release valve which has an alternative arrangement. For example, the leakage aperture in the inlet port may have a channel arrangement similar to the channel formed in the connector 40 described above. Alternatively, the leakage aperture may be formed through the valve itself.

In a further embodiment, the leakage aperture may be formed in the vacuum pump 20. That is, the leakage aperture may be formed in a section of the vacuum pump which forms part of the vacuum path. For example, in one arrangement the leakage aperture is formed in the intake port 21. It will be understood that the intake port 21 is arranged so that the tube 4 does not block the leakage aperture. For example, the intake port may have a shoulder to prevent the tube overlapping the aperture. In such an arrangement, the discharge port 22 may be arranged to direct discharged air over the leakage aperture. The leakage aperture may be a hole or a channel similar to the arrangements described in the above embodiments.

In an alternative embodiment, the leakage aperture may be formed in the hose 4, the vacuum port 13 of the breast pump 2 or the chamber 12 of the breast pump 2, or another suitable position.

Although in the above described embodiments the leakage aperture is a hole or a channel, it will be understood alternative arrangements of the leakage aperture are envisaged in which air is able to flow from atmosphere to the vacuum path through the leakage aperture to release a vacuum in the vacuum path.

Although in the above described embodiments the leakage aperture is a single hole or channel, it will be understood that alternative arrangements are possible. For example, the leakage aperture may be formed from a plurality of holes or channels.

In the above described embodiments the leakage aperture is a hole or channel formed in a component. However, it will be understood that the leakage aperture may be formed from an insert which is receivable in another component, such as the tube 50. In such an arrangement, the insert may be a hollow needle with a bore formed therethrough. The insert is fixedly mounted in the tube so that the bore communicates between the vacuum path and atmosphere. The bore defines the leakage aperture. The bore enables the area of the leakage aperture to be manufactured to a tight tolerance during manufacture. Furthermore, the insert prevents restriction of the leakage aperture due to deformation of the tube.

Although in the above described embodiments the pump unit is provided with separate means for generating the pressure reduction in the vacuum path and releasing the pressure reduction in the vacuum path, it will be understood that they may be integrated. In another embodiment, the pump unit comprises a piston slidably received in a piston chamber or cylinder. The piston acts as a reciprocating element. The piston forms a fluid seal in the chamber. The piston chamber forms part of the vacuum path. The piston is reciprocally operated, for example, by a crankshaft and a motor. When the piston is drawn along the piston chamber, the movement of the piston acts to generate a pressure reduction in the vacuum path. Therefore, a vacuum may be produced at the user's breast. When the piston moves in the opposite on its return stroke the pressure reduction in the chamber is released. However, in the event that the piston becomes stuck or the motor fails, for example, then the piston will not release the pressure reduction in the vacuum path. That is, the pump unit will fail to release the pressure reduction in the vacuum path. If this occurs, then the leakage aperture provided in the vacuum path will allow a controlled release of the pressure reduction in the vacuum path.

In the above embodiment, it will be understood that the vacuum path is formed between the piston and a user's breast when the breast pump system is assembled and a user's breast is received in the funnel. The pump unit may be disposed in the operating unit or may be housed in the breast pump.

In another embodiment, the pump unit is formed by the membrane and a means of mechanically deforming the membrane. The membrane acts as a reciprocating element. For example, a rod may be attached to the deformable membrane which is movable in a reciprocal manner by a motor. With such an arrangement the deformation of the membrane from its neutral condition generates a pressure reduction in the vacuum path. Subsequently, the return of the membrane to its neutral condition releases the pressure reduction in the vacuum path. In this embodiment it will be understood that the vacuum path is formed between the membrane and a user's breast when the breast pump system is assembled and a user's breast is received in the funnel. However, in the event that the membrane does not return to its neutral condition, for example due to failure of the motor, then the membrane will not release the pressure reduction in the vacuum path. That is, the pump unit will fail to release the pressure reduction in the vacuum path. If this occurs, then the leakage aperture provided in the vacuum path will allow a controlled release of the pressure reduction in the vacuum path. The membrane may be the membrane described in the above embodiments or may be another membrane disposed separately.

In the above two embodiments, it will be understood that no pressure release valve is required because the reduction in pressure is released by the valve or membrane returning to its neutral position. The neutral position is obtained when there is no pressure differential acting on the membrane.

It is noted that the present invention also relates to a breast pump system comprising a vacuum path for creating a pressure reduction on a breast, wherein at least part of the vacuum path is formed by a tube, a pump unit configured to generate and release a pressure reduction in the vacuum path, a leakage aperture configured to allow a controlled release of a pressure reduction in at least part of the vacuum path so that the pressure reduction in at least part of the vacuum path is released in the event that the pump unit fails to release the pressure reduction in the vacuum path, and a connector to which the tube is attachable, wherein the leakage aperture is formed in the connector. In a practical embodiment, the leakage aperture is a channel formed in the connector, wherein the tube or a hose attachable to the connector to form part of the vacuum path is configured to partially overlap the channel when attached to the connector so that the channel communicates between the vacuum path and atmosphere.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A breast pump system comprising:
    a vacuum path that includes at least a funnel for communicating a pressure reduction on a breast received in the funnel;
    a pump unit configured to generate and release a pressure reduction in the vacuum path, wherein the pump unit includes a vacuum pump configured to generate the pressure reduction in the vacuum path sufficient to obtain a desired operating pressure reduction at the breast to induce milk expression; and
    a leakage aperture that communicates between the vacuum path and atmosphere, wherein the leakage aperture comprises a non-adjustable leakage area configured to (i) allow a continuous controlled release of the pressure reduction in at least part of the vacuum path so that the pressure reduction in at least part of the vacuum path is released within a predetermined maximum time in the event that the pump unit fails to release the pressure reduction in the vacuum path and (ii) to have a non-substantial effect on the reduction of pressure in the vacuum path during a normal operation of the pump unit in generating and releasing the pressure reduction in the vacuum path, wherein the vacuum pump has a discharge port for discharging air drawn from the vacuum path to atmosphere, and wherein the leakage aperture is disposed proximate to the discharge port so that an airflow discharged from the discharge port to atmosphere is directed over an atmosphere side of the leakage aperture.

2. The breast pump system according to claim 1, wherein the pump unit comprises a pressure release valve operable to release a pressure reduction in the vacuum path.

3. The breast pump system according to claim 2, wherein the leakage aperture is formed in the pressure release valve or the vacuum pump.

4. The a breast pump system according to claim 1, wherein at least part of the vacuum path is formed by a tube and the leakage aperture is formed in the tube.

5. The breast pump system according to claim 4, wherein the leakage aperture is formed by a bore extending through a sidewall of the tube.

6. The breast pump system according to claim 4, further comprising a connector to which the tube is attachable and the leakage aperture is formed in the connector.

7. The breast pump system according to claim 6, wherein the leakage aperture is a channel formed in the connector, and wherein the tube or a hose attachable to the connector to form part of the vacuum path is configured to partially overlap the channel when attached to the connector so that the channel communicates between the vacuum path and atmosphere.

8. The breast pump system according to claim 1, further comprising a filter material extending across the leakage aperture.

9. The breast pump system according to claim 1, wherein the leakage aperture is formed by an insert with a bore extending between the vacuum path and atmosphere.

10. The breast pump system according to claim 1, further comprising a chamber forming part of the vacuum path and a membrane disposable in the chamber to separate the vacuum path into a first section and a second section, wherein the membrane is deformable in response to a reduction of pressure in the first section to generate a reduction of pressure in the second section.

11. The breast pump system according to claim 10, wherein the leakage aperture is configured to allow a controlled release of a pressure reduction generated in the first section of the vacuum path.

12. The breast pump system according to claim 1, further comprising an operating unit and an expression unit, wherein the leakage aperture is disposed in the operating unit.

13. The breast pump system according to claim 12, wherein the operating unit comprises a housing, and the leakage aperture is disposed in the housing.

\* \* \* \* \*